United States Patent
Furlan

(10) Patent No.: US 8,926,522 B2
(45) Date of Patent: *Jan. 6, 2015

(54) WEIGHT SCALE WITH ULTRASOUND IMAGING FOR ANKLE DISPLACEMENT MEASUREMENT

(75) Inventor: Patrick Furlan, Hawthorn Woods, IL (US)

(73) Assignee: STMicroelectronics, Inc., Coppell, TX (US)

( * ) Notice: Subject to any disclaimer, the term of this patent is extended or adjusted under 35 U.S.C. 154(b) by 658 days.

This patent is subject to a terminal disclaimer.

(21) Appl. No.: 13/240,139

(22) Filed: Sep. 22, 2011

(65) Prior Publication Data

US 2012/0010504 A1 Jan. 12, 2012

Related U.S. Application Data

(63) Continuation of application No. 12/546,180, filed on Aug. 24, 2009, now Pat. No. 8,048,000.

(60) Provisional application No. 61/091,670, filed on Aug. 25, 2008.

(51) Int. Cl.
| | |
|---|---|
| A61B 5/02 | (2006.01) |
| A61B 5/00 | (2006.01) |
| A61B 5/103 | (2006.01) |
| G01G 19/44 | (2006.01) |
| G01G 23/37 | (2006.01) |

(52) U.S. Cl.
CPC ............... *A61B 5/02* (2013.01); *A61B 5/0002* (2013.01); *A61B 5/103* (2013.01); *A61B 5/4528* (2013.01); *A61B 5/4878* (2013.01); *G01G 19/44* (2013.01); *G01G 23/3728* (2013.01)
USPC ........................................... 600/508

(58) Field of Classification Search
None
See application file for complete search history.

(56) References Cited

U.S. PATENT DOCUMENTS

| | | | | |
|---|---|---|---|---|
| 5,788,643 | A | * | 8/1998 | Feldman ........................ 600/506 |
| 6,080,106 | A | | 6/2000 | Lloyd et al. |
| 6,409,662 | B1 | | 6/2002 | Lloyd et al. |
| 6,512,949 | B1 | | 1/2003 | Combs et al. |
| 6,714,813 | B2 | | 3/2004 | Ishigooka et al. |
| 2001/0020138 | A1 | | 9/2001 | Ishigooka et al. |
| 2005/0192487 | A1 | | 9/2005 | Cosentino et al. |
| 2007/0270707 | A1 | * | 11/2007 | Belalcazar ..................... 600/547 |
| 2008/0082132 | A1 | | 4/2008 | Annest et al. |
| 2008/0262360 | A1 | | 10/2008 | Dalal et al. |
| 2010/0049065 | A1 | | 2/2010 | Furlan |

* cited by examiner

*Primary Examiner* — Kennedy Schaetzle
(74) *Attorney, Agent, or Firm* — Gardere Wynne Sewell LLP

(57) ABSTRACT

A device for correlating trend data with respect to a patient's weight ankle displacement can identify conditions indicative of congestive heart failure. A weight scale or similar device coupled with imaging mechanism operable to measure ankle displacement collects a plurality of measurements over a period of time. Over time trend analysis of both the patient's weight and the ankle displacement measurements can be obtained and compared to identify whether over a particular sample period an increase in a patient's ankle displacement is or is not correlated with an increase in the patient's weight. When an increase in ankle displacement is identified as not correlating to a corresponding change in the patient's weight an alert can be issued of conditions indicative of congestive heart failure.

20 Claims, 4 Drawing Sheets

WEIGHT SCALE WITH ULTRASOUND IMAGING FOR ANKLE DISPLACEMENT MEASUREMENT

CROSS-REFERENCE TO RELATED APPLICATIONS

This application is a continuation of and claims the benefit of U.S. patent application Ser. No. 12/546,180 filed Aug. 24, 2009, issued as U.S. Pat. No. 8,048,000 and claims the benefit of U.S. Provisional Application No. 61/091,670 filed Aug. 25, 2008. The disclosure of the foregoing United States Patent Application is specifically incorporated herein by this reference.

BACKGROUND OF THE INVENTION

1. Field of the Invention

Embodiments of the present invention relate, in general to home healthcare monitoring and more particularly to monitoring and correlating trend data with respect to ankle displacement measurements and patient weight and thereafter transmitting that data to a healthcare professional when a statistically significant event occurs.

2. Relevant Background

Congestive heart failure, or heart failure, is a condition in which the heart cannot pump enough blood to the body's other organs. This can result from a variety of causes including narrowed arteries that supply blood to the heart muscle, coronary artery disease, scar tissue build up from past heart attack or myocardial infarction that interferes with the heart muscle's normal work, high blood pressure, heart valve disease due to past rheumatic fever or other causes, heart defects present at birth, and infection of the heart valves and/or heart muscle itself.

Congestive heart failure is a condition in which the heart, while continuing to function, does not perform its work as efficiently as it should. People with heart failure cannot exert themselves because they become short of breath and fatigued. As blood flow out of the heart slows, blood returning to the heart through the veins backs up, causing congestion in the tissues. Often swelling (edema) results. Most often there is swelling in the legs and ankles, but swelling can occur in other parts of the body as well. Sometimes fluid collects in the lungs and interferes with breathing, causing shortness of breath, especially when a person is lying down. Another common symptom is swelling in lower extremities, especially the feet and ankles.

The degree of swelling people with heart failure experience depends on how well their body is compensating for the heart failure and how much sodium and water their body retains. In some cases the swelling is mild and merely bothersome, while in other cases it can be severe and painful as their skin becomes taut and sensitive.

The medical term for this swelling in the legs is pedal edema—"pedal" refers to the feet and "edema" refers to the buildup of excess fluid. Heart failure often causes what doctors call "pitting edema," meaning that applying pressure to the swollen skin leaves an indentation in the skin. Doctors often test for edema by pressing their thumb to the skin and seeing whether it leaves an impression. One common example of pitting edema is when, upon removal of one's footwear, he or she discovers that his or her socks have left an impression in the skin of the ankles and feet. However, tests such as this are used to confirm extreme cases of edema after a patient has sought assistance. The presence of edema is used to verify or support a diagnosis rather than proactively to identify a potential or growing condition.

While the association of pedal edema and heart failure is well known, the presence of pedal edema in a patient experiencing heart failure is typically one of many factors used to reach a diagnosis once a patient has sought out medical care. For example a chest X-ray indicating a build up of fluid in the cavity surrounding the lungs resulting in the patient experiencing difficulty in breathing may also be indicative of heart failure. But unlike blood tests, X-rays and other non-ambulatory tests, pedal edema can be readily observed and monitored by the patient.

However, even when patients having a high likelihood or susceptibility to heart failure are asked to monitor various physiological conditions including pedal edema, patient compliance is historically poor and unreliable. A need therefore exists for a system and apparatus to efficiently and effortlessly monitor changes in pedal edema of a patient showing susceptibility to heart failure. Furthermore there is a need to record such data and correlate it with the weight of a patient over a period of time so as to determine whether any changes in pedal edema are consistent or inconsistent with weight change. Finally a need remains to convey this information to a healthcare professional for analysis and, if necessary, to initiate proactive measures to minimize risk to the patient. These and other improvements to the prior art are hereafter described by way of example.

SUMMARY OF THE INVENTION

The present invention, described hereafter by way of example, provides a system and method for correlating trend data with respect to a patient's weight with trend data with respect to the patient's ankle displacement. According to one embodiment of the present invention, a device incorporates both a weight scale and ultrasound or similar imaging mechanism to measure ankle displacement. Over time trend analysis of both the patient's weight and the ankle displacement measurements can be obtained and compared to identify whether an increase in a patient's ankle displacement is or is not correlated with an increase in the patient's weight.

According to one embodiment of the present invention a scale or similar device incorporates an electronic measuring apparatus using technology such as ultrasound, infrared or other means to measure ankle displacement by way of imaging. The collected data is then processed by a microprocessor. The microprocessor, using a correlation module and the trend analysis module, determines whether there is a statistically unique difference in trend data for a patient's weight and ankle displacement. Upon determination that a statistical variance in the data has occurred, and according to one embodiment of present invention, a healthcare professional can be alerted and, if necessary, steps can be taken to contact the patient to render advice or treatment.

According to another embodiment of the present invention, a device collects data with respect to the patient's weight and ankle displacement. The data is thereafter stored and trend analysis is conducted on both the patient's weight and ankle displacement measurements. Trends of the patient's weight and measurements of the patient's ankle displacements are examined and a correlation can be determined between the two sets of data. If there is a low correlation, meaning that ankle displacement measurements show a trend that is minimally related to the patient's weight measurements, an alert is sent to a medical or healthcare professional for further analysis. According to another embodiment of the present invention, the data can be transmitted via a network such as the Internet or other wide-area network or the data can be used to alert the patient via a display or similar device.

The features and advantages described in this disclosure and in the following detailed description are not all-inclusive. Many additional features and advantages will be apparent to one of ordinary skill in the relevant art in view of the drawings, specification, and claims hereof. Moreover, it should be noted that the language used in the specification has been principally selected for readability and instructional purposes and may not have been selected to delineate or circumscribe the inventive subject matter; reference to the claims is necessary to determine such inventive subject matter.

BRIEF DESCRIPTION OF THE DRAWINGS

The aforementioned and other features and objects of the present invention and the manner of attaining them will become more apparent, and the invention itself will be best understood, by reference to the following description of one or more embodiments taken in conjunction with the accompanying drawings, wherein.

Figure 1:
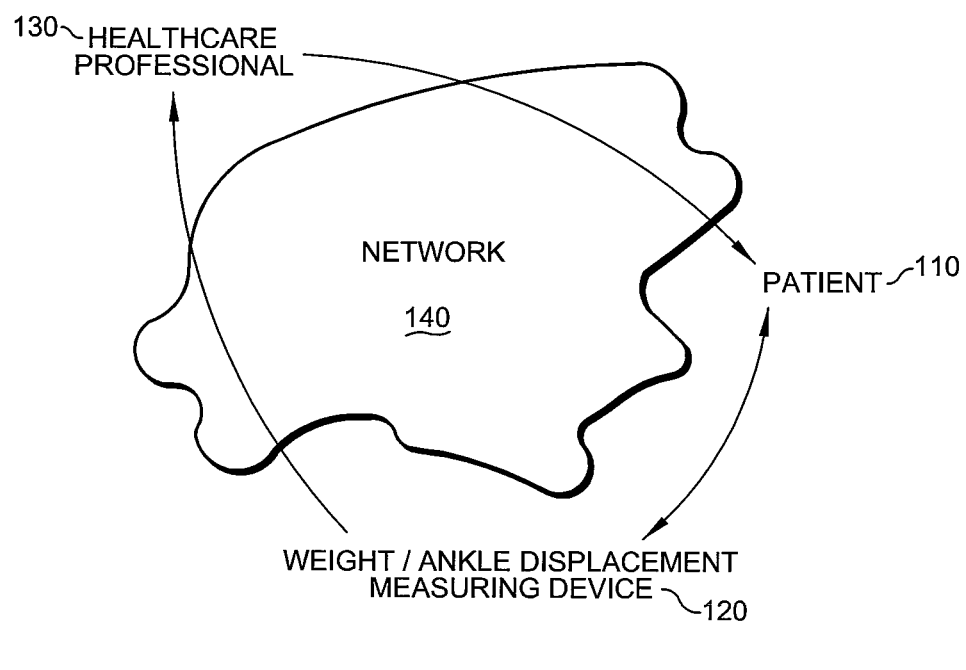
FIG. 1 is a high-level system diagram showing the relationship between a patient and ankle displacement measurement device, and a healthcare professional.

The Figures depict embodiments of the present invention for purposes of illustration only. One skilled in the art will readily recognize from the following discussion that alternative embodiments of the structures and methods illustrated herein may be employed without departing from the principles of the invention described herein.

DESCRIPTION OF THE INVENTION

Embodiments of the present invention are hereafter described in detail with reference to the accompanying Figures. Although the invention has been described and illustrated with a certain degree of particularity, it is understood that the present disclosure has been made only by way of example and that numerous changes in the combination and arrangement of parts can be resorted to by those skilled in the art without departing from the spirit and scope of the invention.

One of the leading causes of death relating to cardiac disease is congestive heart failure. This condition can be monitored in various ways including echocardiograms, weight monitoring and measurements of pedal edema. As discussed herein, pedal edema is a condition where the lower extremities of the human body swell due to the accumulation of fluid. As the heart becomes inefficient fluid collects in the lower extremities, including the feet and ankles, causing them to swell. There are number of reasons why a patient may experience swelling of the lower extremities. These reasons include injuries such as ankle sprains or general immobility due to some other type of illness or injury. However, when it is not associated with other contraindicated symptoms, pedal edema may be indicative of congestive heart failure. A statistically significant change in a patient's ankle displacement without a similar statistically significant change in the patient's weight may be an early indication of pedal edema associated with congestive heart failure.

According to one embodiment of the present invention, a device incorporates the ability to measure and store both a patient's weight and ankle displacement or size of the patient's ankles. Simultaneous measurement of both the patient's weight and ankle displacement is taken and stored for further analysis by the simple act of a patient stepping on a scale. Over time trend information for both the patient's weight and ankle displacement is determined and compared so that a correlation factor can be calculated. If the size of the patient's ankles increases over time, as indicated by the ankle displacement trend data, without a corresponding variance in the patient's weight, a low correlation factor is determined. This low correlation or non-correlating factor can be indicative of congestive heart failure. The displacement or size of a healthy individual's ankles does not significantly vary from one day to another. And when such a variation is noted it is typically associated with a corresponding gain in weight. For example, a person who generally maintains a low sodium diet may find their weight fluctuate 2-5 lbs due to a meal having a high salt content. This weight gain, which is primarily due to water, may cause a corresponding swelling in the ankles. Similarly, weight gain over a prolonged period to time may also be associated with increased ankle displacement. This type of correlated variance in a person's weight and ankle size would not be indicative of congestive heart failure. However an uncorrelated increase in ankle displacement may warrant further scrutiny.

When the present invention determines a low or non-correlating factor between the patient's historical weight data and the patient's historical ankle displacement data, a message is sent to a healthcare professional for further analysis and, if necessary, proactive action. The healthcare professional can thereafter contact the patient, ask additional questions and, if necessary, direct him or her to a hospital or similar facility for further testing. According to another embodiment of the present invention, a display device can provide a patient directly with healthcare protocols and/or advice directing him or her to a hospital or similar facility.

FIG. 1 shows a high-level view of a system for correlating trend data regarding a patient's weight with that regarding their ankle displacement. A patient 110 utilizes a weight and an ankle displacement measuring device 120 to measure both their weight and ankle size simultaneously. Each time the patient utilizes the device 120 data is collected and stored for further analysis. According to one embodiment of the present invention, data collected over time by the ankle displacement measuring device 120 is conveyed via a network 140 to a healthcare professional 130 for further analysis. According to another embodiment of the present invention, the device 120 collects and stores data within the device and thereafter processes the information to determine whether trend data with respect to the patient's weight and the patient's ankle displacement measurements are statistically correlated. When a non-correlating event occurs in which a patient's ankles swell without a corresponding change in weight, the device 120 transmits or conveys that information via a network 140 to a healthcare professional 130. The healthcare professional 130 thereafter can contact the patient 110 for further action including directing the patient to a hospital or other healthcare facility for further testing.

Figure 2:
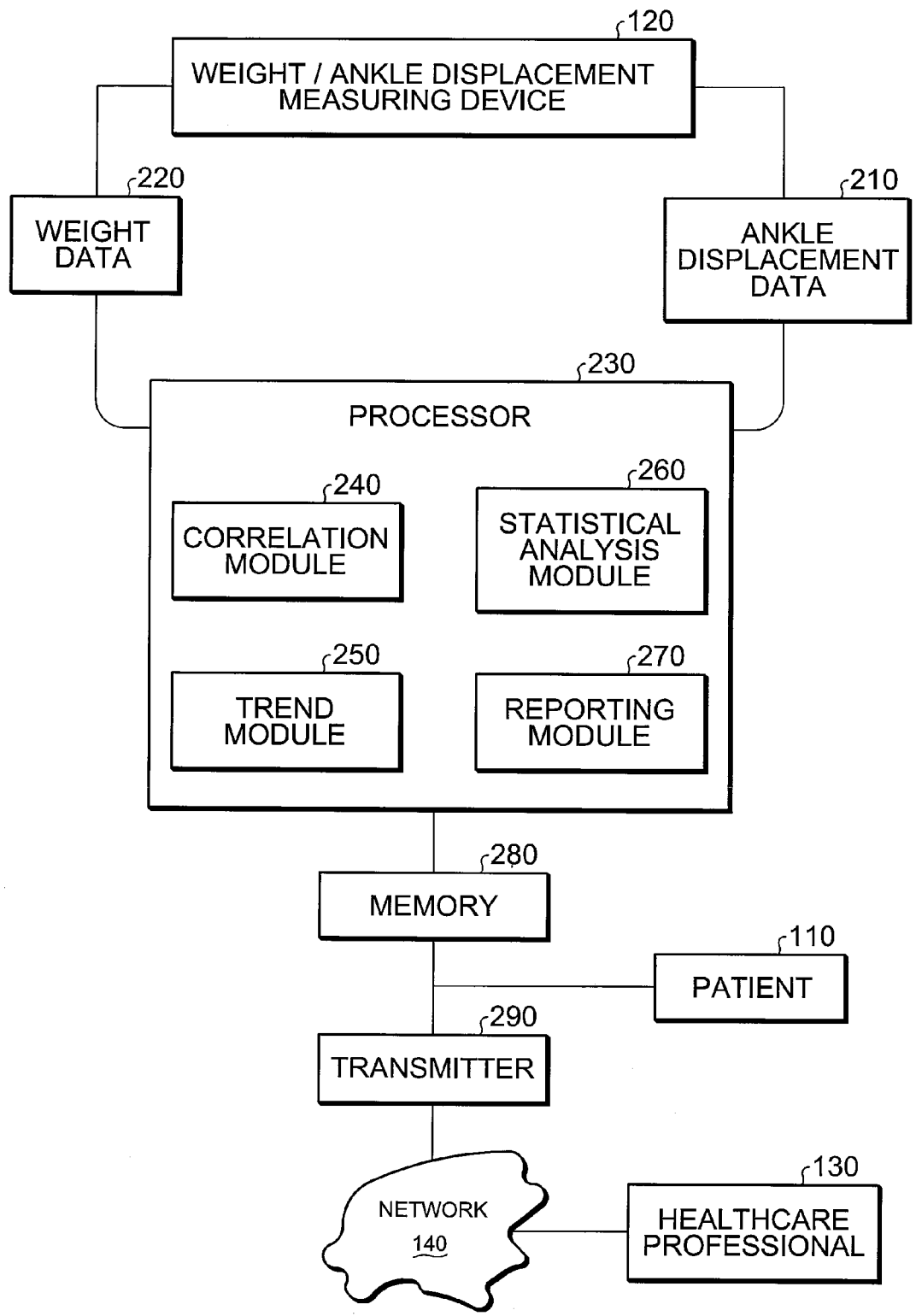
FIG. 2 is a high-level component diagram showing the relationship between various components of a weight scale and ankle displacement measurement device according to one embodiment of the present invention.

FIG. 2 is a high-level system diagram of components of one embodiment of an ankle displacement and weight measuring device. According to one embodiment of the present invention, the weight and ankle displacement measuring device 120 includes a patient interface 200 on which the patient stands and that includes a scale and some means to measure ankle size. As will be appreciated by one skilled in the relevant art, a number of means can be used to measure both the patient's weight and ankle size. For example electronic scales that are well known in the prior art measure a patient's weight using strain gauges and other weight measuring devices. It is also well known that body composition measurements can be conducted by measuring impedance of a small electrical charge passed through the body. Similarly, a patient's ankle size can be accurately measured using ultrasound, infrared, or other electronic means as would be known to one skilled in the relevant art. Each of these and other technical means to measure ankle displacement are contemplated by the present invention.

As shown in FIG. 2, the weight and ankle displacement measuring interface 200 is coupled to memory for storage of weight data 220 and ankle displacement measurements 210. Upon the collection of historical data a processor 230 accesses the patient's weight data 220 and historical ankle measurement data 210 to conduct, using trend module 250, a respective trend analysis. This trend data is then processed by a correlation module 240 and a statistical analysis module 260 to determine whether the historical data of the patient's weight and historical data with respect to a patient's ankle size are correlated.

According to one embodiment of the present invention, when the trend data of size of a patient's ankles is not correlated with the trend data of the patient's weight, a report is generated by the reporting module 270. The event is recorded in memory 280 and transmitted via a transmitting module 290 and network 140 to a healthcare professional 130. For example, assume a patient with a history of heart disease has been directed to use one embodiment of the present invention on a routine basis. After some baseline measurements the patient is sent home with the device. Over a prolonged period of time, say 6 months, the patient regularly steps onto the device and the device automatically records the patient's weight and ankle displacement. The data is collected, and upon the collection of enough data points to make a statistical analysis, trends are analyzed. The process is ongoing and each time the patient steps onto the scale the historical data and trend analysis are revised. Normally the patient's weight and ankle displacement would show a high degree of correlation. However, if an unexplained increase in the person's ankles occurs without any corresponding weight increase, the present invention identifies this uncorrelated event and reports it to a healthcare professional and/or the patient.

According to another embodiment of the present invention, responsive to the determination of a low correlation factor between historical measurements of a patient's weight and the patient's ankle size over a predetermined sampling period, the present invention can institute a series of questions or inquiries to narrow the instances of false positive alerts. A false positive is a condition in which, while a low correlation between the patient's weight and ankle size over the sampling period does exist, the causes of the that low correlation may be easily explained. For example, if a statistically significant event was identified shortly after the person experienced an ankle injury then the low correlation factor may not be an indication of congestive heart failure. Also if ankle displacement measurements indicate only an increase of size of one ankle versus both ankles the protocols can be programmed to inquire if an injury has occurred.

In a preferred embodiment, at least a portion of the present invention can be implemented in software. Software programming code which embodies the present invention is typically accessed by a microprocessor 230 from long-term, persistent storage media of some type, such as a flash drive or hard drive. The software programming code may be embodied on any of a variety of known media for use with a data processing system, such as a diskette, hard drive, or CD-ROM. The code may be distributed on such media, or may be distributed from the memory or storage of one computer system over a network of some type to other computer systems for use by such other systems. Alternatively, the programming code may be embodied in the memory of the device and accessed by a microprocessor using an internal bus. The techniques and methods for embodying software programming code in memory, on physical media, and/or distributing software code via networks are well known and will not be further discussed herein.

Generally, program modules include routines, programs, objects, components, data structures and the like that perform particular tasks or implement particular abstract data types. Moreover, those skilled in the art will appreciate that the invention can be practiced with other computer system configurations, including hand-held devices, multi-processor systems, microprocessor-based or programmable consumer electronics, network PCs, minicomputers, mainframe computers and the like. The invention may also be practiced in distributed computing environments where tasks are performed by remote processing devices that are linked through a communications network. In a distributed computing environment, program modules may be located in both local and remote memory storage devices.

An exemplary system for implementing the invention includes a general purpose computing device in the form of a conventional personal computer, a personal communication device or the like, including a processing unit, a system memory, and a system bus that couples various system components including the system memory to the processing unit. The system bus may be any of several types of bus structures including a memory bus or memory controller, a peripheral bus, and a local bus using any of a variety of bus architectures. The system memory generally includes read-only memory (ROM) and random access memory (RAM). A basic input/output system (BIOS), containing the basic routines that help to transfer information between elements within the personal computer, such as during start-up, is stored in ROM. The personal computer may further include a hard disk drive for reading from and writing to a hard disk, a magnetic disk drive for reading from or writing to a removable magnetic disk. The hard disk drive and magnetic disk drive are connected to the system bus by a hard disk drive interface and a magnetic disk drive interface, respectively. The drives and their associated computer-readable media provide non-volatile storage of computer readable instructions, data structures, program modules and other data for the personal computer. Although the exemplary environment described herein employs a hard disk and a removable magnetic disk, it should be appreciated by those skilled in the art that other types of computer readable media which can store data that is accessible by a computer, such as magnetic cassettes, flash memory cards, digital video disks, random access memories (RAMs), read-only memories (ROMs) and the like may also be used in the exemplary operating environment.

A number of program modules may be stored on the hard disk, magnetic disk, ROM or RAM, including an operating system, one or more application programs or software portions, other program modules and program data. A user may enter commands and information into the personal computer through input devices such as a keyboard and pointing device. Other input devices may include a microphone, joystick, game pad, satellite dish, scanner or the like. These and other input devices are often connected to the processing unit through a serial port interface that is coupled to the system bus, but may be connected by other interfaces, such as a parallel port, game port or universal serial bus (USB). A monitor or other type of display device may also be connected to the system bus via an interface, such as a video adapter.

A personal computer or processor such as one employed in the present invention may operate in a networked environment using logical connections to one or more remote computers. The remote computer may be another personal computer, a server, a router, a network PC, a peer device or other common network node, and typically includes many or all of the elements described above relative to the personal computer. The logical connections described herein include local area networks (LAN) and a wide area networks (WAN). Such networking environments are commonplace in offices, enterprise-wide computer networks, Intranets and the Internet.

When used in a LAN networking environment, the computer is connected to the local network through a network interface or adapter. When used in a WAN networking environment, the computer typically includes a means for establishing communications over the wide area network, such as the Internet. This means is connected to the system bus via the serial port interface. In a networked environment, program modules depicted relative to the personal computer, or portions thereof, may be stored in the remote memory storage device. It will be appreciated that the network connections shown are exemplary and other means of establishing a communications link between the computers may be used.

Included in the description are flowcharts depicting examples of the methodology which may be used to correlate trend data between a patient's weight and ankle displacement measurements. In the following description, it will be understood that each block of the flowchart illustrations, and combinations of blocks in the flowchart illustrations, can be implemented by computer program instructions. These computer program instructions may be loaded onto a computer or other programmable apparatus to produce a machine such that the instructions that execute on the computer or other programmable apparatus create means for implementing the functions specified in the flowchart block or blocks. These computer program instructions may also be stored in a computer-readable memory that can direct a computer or other programmable apparatus to function in a particular manner such that the instructions stored in the computer-readable memory produce an article of manufacture including instruction means that implement the function specified in the flowchart block or blocks. The computer program instructions may also be loaded onto a computer or other programmable apparatus to cause a series of operational steps to be performed in the computer or on the other programmable apparatus to produce a computer implemented process such that the instructions that execute on the computer or other programmable apparatus provide steps for implementing the functions specified in the flowchart block or blocks.

Accordingly, blocks of the flowchart illustrations support combinations of means for performing the specified functions and combinations of steps for performing the specified functions. It will also be understood that each block of the flowchart illustrations, and combinations of blocks in the flowchart illustrations, can be implemented by special purpose hardware-based computer systems that perform the specified functions or steps, or combinations of special purpose hardware and computer instructions.

Figure 3A:
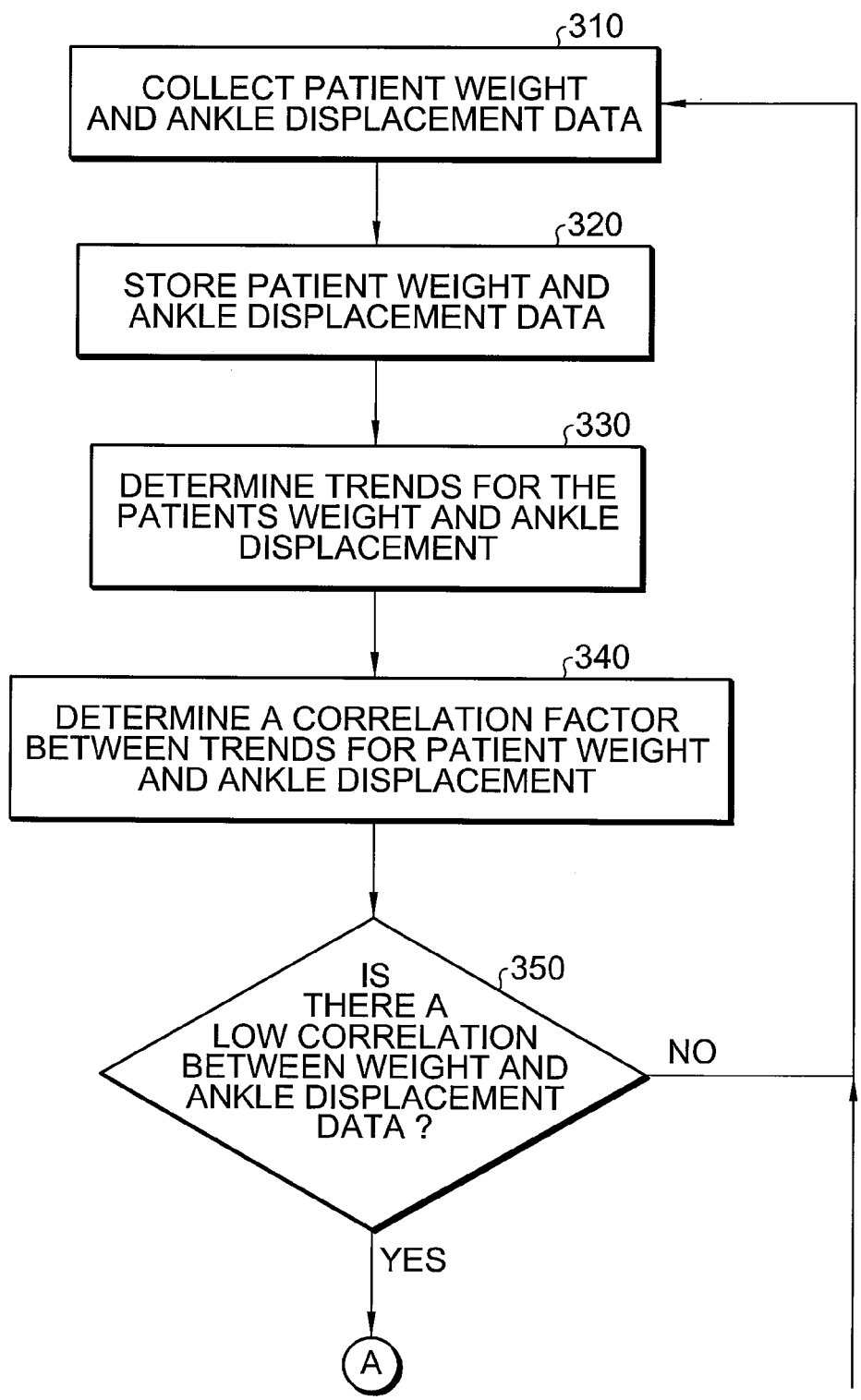
FIG. 3 is a method embodiment for determining correlation between a patient's weight and ankle displacement measurements according to the present invention.
Figure 3B:
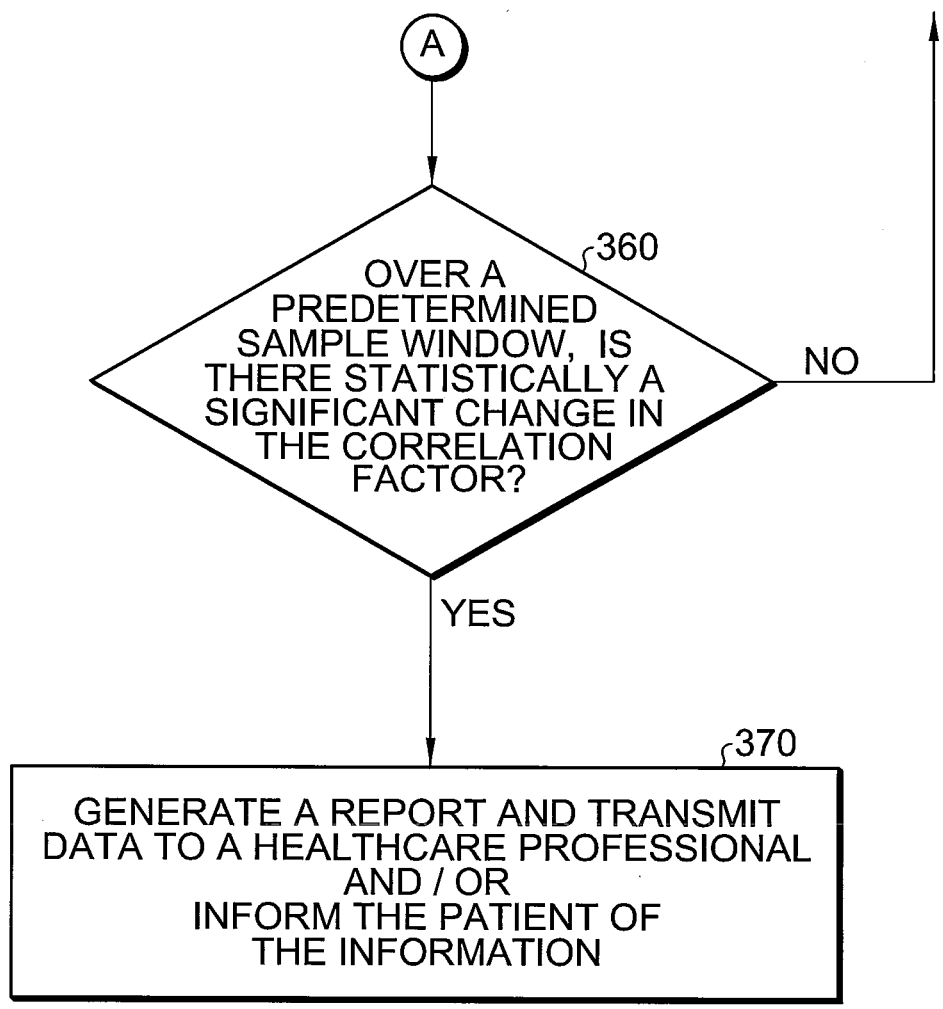

According to one embodiment of the present invention, a determination with respect to correlation between a patient's weight and a patient's ankle size can be made by specifically analyzing trend data over a period of time. FIG. 3 shows the flowchart of one method embodiment for determining correlation data between the patient's weight and ankle displacement measurements. The process begins with collection 310 of a patient's weight and ankle displacement. The respective data is thereafter stored 320 on a persistent memory device as would be known to one skilled in the relevant art. Trend analysis is conducted to determine 330 a historical image of the patient's weight and ankle displacement measurements, and thereafter the two sets of data are compared to determine 340 whether a correlation factor exists.

A query 350 is then made whether the correlation factor for a local event is a large number or a small number. If the correlation factor is large, indicating a correlation between the variances in trend data of the patient's weight and the ankle displacement measurements, data is continued to be collected and analyzed.

When the correlation factor is small, indicating that the variance in the patient's ankle displacement measurements is not correlated with the variance in the patient's weight, the present invention determines whether data is sufficient to consider if the analysis is indicative of congestive heart failure. Thereafter another query 360 is conducted to determine whether the correlation factor is statistically significant. For example, a gradual change in ankle size may be dismissed while a rapid change in ankle displacement, as indicated by a statistically significant change in the correlation factor, may warrant further analysis. The second query 360, therefore, determines whether the change in the ankle displacement measurements as compared to the change in the patient's weight is so significantly different as to rule out other possible factors which may explain the change in size of the patient's ankle. When it is concluded that the statistically significant change is likely indicative of pedal edema associated with congestive heart failure, a report so indicating is generated.

Thereafter, the data is transmitted 370 to a healthcare professional for further analysis. According to another embodiment of the present invention, when the analysis of the trend data reveals a statistically significant change in the ankle displacement measurements a report is generated, which is conveyed directly to the patient. Whether the data is transmitted to a healthcare professional or conveyed to the patient via a display device, the present invention provides important information to a patient with respect to a significant change in their anatomy which may be indicative of congestive heart failure.

As will be understood by those familiar with the art, the invention may be embodied in other specific forms without departing from the spirit or essential characteristics thereof. Likewise, the particular naming and division of the modules, managers, functions, systems, engines, layers, features, attributes, methodologies, and other aspects are not mandatory or significant, and the mechanisms that implement the invention or its features may have different names, divisions, and/or formats. Furthermore, as will be apparent to one of ordinary skill in the relevant art, the modules, managers, functions, systems, engines, layers, features, attributes, methodologies, and other aspects of the invention can be implemented as software, hardware, firmware, or any combination of the three. Of course, wherever a component of the present invention is implemented as software, the component can be implemented as a script, as a standalone program, as part of a larger program, as a plurality of separate scripts and/or programs, as a statically or dynamically linked library, as a kernel loadable module, as a device driver, and/or in every and any other way known now or in the future to those of skill in the art of computer programming. Additionally, the present invention is in no way limited to implementation in any specific programming language, or for any specific operating system or environment. Accordingly, the disclosure of the present invention is intended to be illustrative, but not limiting, of the scope of the invention, which is set forth in the following claims.

While there have been described above the principles of the present invention in conjunction with a weight scale and ankle displacement measurement device, it is to be clearly understood that the foregoing description is made only by way of example and not as a limitation to the scope of the invention. Particularly, it is recognized that the teachings of the foregoing disclosure will suggest other modifications to those persons skilled in the relevant art. Such modifications may involve other features that are already known per se and which may be used instead of or in addition to features already described herein. Although claims have been formulated in this application to particular combinations of features, it should be understood that the scope of the disclosure herein also includes any novel feature or any novel combination of features disclosed either explicitly or implicitly or any generalization or modification thereof which would be apparent to persons skilled in the relevant art, whether or not such relates to the same invention as presently claimed in any claim and whether or not it mitigates any or all of the same technical problems as confronted by the present invention. The Applicant hereby reserves the right to formulate new claims to such features and/or combinations of such features during the prosecution of the present application or of any further application derived therefrom.

The invention claimed is:

1. An apparatus for correlating ankle displacement with weight, the apparatus comprising:
   a processor containing:
      program code configured to calculate a weight measurement trend and an ankle displacement measurement trend,
      program code configured to determine a correlation factor between the weight measurement trend and the ankle displacement trend, and
      responsive to the correlation factor being below a predetermined value, program code to determine whether the correlation factor being below the predetermined value is statistically significant.

2. The apparatus of claim 1 further comprising an ankle displacement device that uses ultrasound waves to measure ankle displacement.

3. The apparatus of claim 1 further comprising an ankle displacement device that uses infrared waves to measure ankle displacement.

4. The apparatus of claim 1 further comprising a transmitter operable to wirelessly transmit an alert to a healthcare professional responsive to the correlation factor being below the predetermined value and being statistically significant.

5. The apparatus of claim 1 further comprising a display operable to display an alert when the correlation factor is below the predetermined value and is statistically significant.

6. The apparatus of claim 1 wherein the processor is coupled to a network and wherein the processor is operable to transmit an alert via the network to a healthcare professional responsive to the correlation factor being below the predetermined value and being statistically significant.

7. The apparatus of claim 1 further comprising program code configured to, responsive to the correlation factor being below the predetermined value being statistically significant, create an alert.

8. The apparatus of claim 7 further comprising program code configured to automatically convey the alert to a healthcare professional.

9. The apparatus of claim 7 further comprising program code configured to inform the user of the alert.

10. A method for monitoring correlation between a patient's weight and ankle displacement, the method comprising:
    determining a plurality of weight measurements and a plurality of ankle displacement measurements;
    calculating a weight measurement trend and an ankle displacement measurement trend;
    determining a correlation factor between the weight measurement trend and the ankle displacement measurement trend; and
    responsive to the correlation factor being below a predetermined value, issuing an alert message.

11. The method of claim 10 wherein the ankle displacement measurement and the weight measurement are taken substantially simultaneously.

12. The method of claim 10 wherein the alert is automatically conveyed to a healthcare professional.

13. The method of claim 10 wherein the alert is automatically displayed to the patient.

14. The method of claim 10 wherein each of the plurality of ankle displacement measurements is determined using ultrasound waves.

15. The method of claim 10 wherein each of the plurality of ankle displacement measurements is determined using infrared technology.

16. The method of claim 10 further comprising, responsive to issuing an alert message, presenting to the patient a plurality of questions and wherein based on the response to the plurality of questions determining whether a healthcare professional should be automatically alerted.

17. A home healthcare monitoring device usable by a patient for determining conditions indicative of congestive heart failure, the device comprising:
    a processor coupled to the memory and capable of executing a program of instructions wherein said program of instructions comprises a plurality of program codes for determining correlation between a plurality of ankle displacement measurements and a plurality of weight measurements, wherein said program of instructions includes
       program code configured to calculate a weight measurement trend and an ankle displacement measurement trend,
       program code configured to determine a correlation factor between the weight measurement trend and the ankle displacement trend, and
       responsive to the correlation factor being below a predetermined value, program code to create an alert of a condition indicative of congestive heart failure.

18. The home healthcare monitoring device of claim 17 wherein the plurality of ankle measurements includes measurements made using ultrasound waves.

19. The home healthcare monitoring device of claim 17 wherein the plurality of ankle measurements includes measurements made using infrared technology.

20. The home healthcare monitoring device of claim 17 wherein responsive to the correlation factor being below a predetermined value, the program code to create an alert includes a plurality of questions for presentation to the patient and wherein based on the response to the plurality of questions, a determination is made whether a healthcare professional should be automatically alerted.

* * * * *